US011548524B2

(12) United States Patent
Park

(10) Patent No.: US 11,548,524 B2
(45) Date of Patent: Jan. 10, 2023

(54) VEHICLE AND METHOD OF CONTROLLING THE SAME

(71) Applicants: Hyundai Motor Company, Seoul (KR); Kia Corporation, Seoul (KR)

(72) Inventor: Sung Joon Park, Gwangmyeong-si (KR)

(73) Assignees: Hyundai Motor Company, Seoul (KR); Kia Corporation, Seoul (KR)

( * ) Notice: Subject to any disclaimer, the term of this patent is extended or adjusted under 35 U.S.C. 154(b) by 0 days.

(21) Appl. No.: 17/493,052

(22) Filed: Oct. 4, 2021

(65) Prior Publication Data

US 2022/0144299 A1    May 12, 2022

(30) Foreign Application Priority Data

Nov. 12, 2020  (KR) .......................... 10-2020-0150990

(51) Int. Cl.
*B60W 50/14* (2020.01)
*B60W 40/08* (2012.01)

(52) U.S. Cl.
CPC ............ *B60W 50/14* (2013.01); *B60W 40/08* (2013.01); *B60W 2040/0827* (2013.01); *B60W 2040/0872* (2013.01); *B60W 2050/143* (2013.01); *B60W 2400/00* (2013.01); *B60W 2540/221* (2020.02); *B60W 2540/229* (2020.02); *B60W 2710/30* (2013.01); *B60W 2756/10* (2020.02)

(58) Field of Classification Search
None
See application file for complete search history.

(56) References Cited

U.S. PATENT DOCUMENTS

| 9,988,055 B1* | 6/2018 | O'Flaherty ............ G08B 21/06 |
| 2007/0282506 A1* | 12/2007 | Breed ................... G06V 10/143 |
| | | 701/45 |
| 2016/0217672 A1* | 7/2016 | Yoon .................... A61B 5/4818 |
| 2017/0325701 A1* | 11/2017 | Castro Miller ........ A61B 5/349 |
| 2018/0079278 A1 | 3/2018 | Kirpichnikov et al. |

FOREIGN PATENT DOCUMENTS

| KR | 20170137832 A | 12/2017 |
| KR | 102054213 B1 | 12/2019 |

OTHER PUBLICATIONS

Douglas, Neil J., et al., "Respiration during sleep in normal man", Thorax, vol. 37, published Nov. 1, 1982, pp. 840-844.

\* cited by examiner

*Primary Examiner* — Thomas S McCormack
(74) *Attorney, Agent, or Firm* — Slater Matsil, LLP

(57) ABSTRACT

A vehicle includes a first sensor configured to measure a respiration temperature, a facial temperature, and a heart temperature of a user, a second sensor configured to measure a carbon dioxide concentration in a respiration of the user, and a controller configured to determine a respiration volume and a respiration cycle of the user based on the first sensor, based on the measured carbon dioxide concentration in the respiration being greater than or equal to a predetermined carbon dioxide concentration, compare each of the respiration volume and the respiration cycle with a predetermined respiration volume and a predetermined respiration cycle, and based on the comparison result, output an alarm signal corresponding to each state of an awakening state or a sleeping state in response to a determination that the user is in the awakening state or the sleeping state.

20 Claims, 6 Drawing Sheets

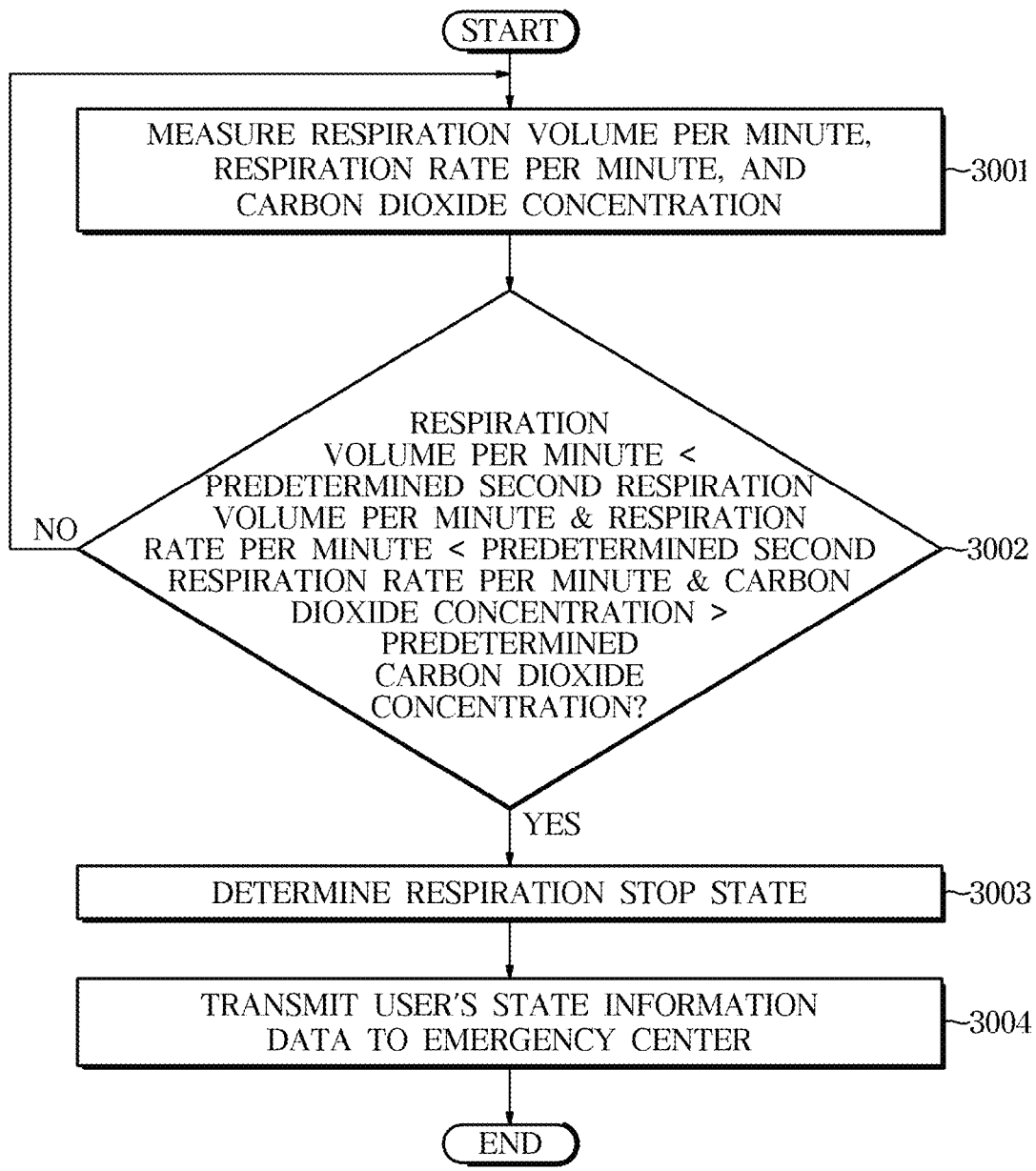

VEHICLE AND METHOD OF CONTROLLING THE SAME

CROSS-REFERENCE TO RELATED APPLICATIONS

This application claims the benefit of Korean Patent Application No. 10-2020-0150990, filed on Nov. 12, 2020, which application is hereby incorporated herein by reference.

TECHNICAL FIELD

The disclosure relates to a vehicle and a method of controlling the vehicle.

BACKGROUND

A thermal imaging camera is a device that tracks and detects heat and displays it on a screen at a glance. General cameras have the same structure as human eyes, so they capture a similar image to what our eyes see, but thermal imaging cameras are special equipment that only use the heat to capture. Taking advantage of these points, the thermal imaging cameras have been usefully used in various fields in recent years. In some cases, drones are equipped with the thermal imaging cameras to monitor forest fires and to easily determine whether livestock is diseased.

Recently, traffic accidents caused by drowsy driving are increasing. Accordingly, research is being actively conducted to prevent drowsy driving. A method of incorporating a technology for determining whether a user is sleeping using the thermal imaging camera may be considered in this technical field.

By analyzing an inhalation and an exhalation exhaled by the user through the thermal imaging camera, it is possible to determine whether it corresponds to a sleeping state, and apply this to the driving user.

SUMMARY

The disclosure relates to a vehicle and a method of controlling the vehicle. Particular embodiments relate to a vehicle for determining whether a user corresponds to a sleeping state, and a method of controlling the vehicle.

An embodiment of the disclosure provides a vehicle that calculates a user's respiration cycle and respiration volume through a thermal imaging camera, determines whether the user corresponds to a sleeping state, and outputs an alarm signal, and a method of controlling the vehicle.

Additional embodiments of the disclosure will be set forth in part in the description which follows and, in part, will be obvious from the description, or may be learned by practice of the disclosure.

According to an embodiment of the disclosure, there is provided a vehicle including a first sensor configured to measure a user's respiration temperature, a user's facial temperature, and a user's heart temperature, a second sensor configured to measure a carbon dioxide concentration in a user's respiration, and a controller configured to determine a user's respiration volume and respiration cycle based on the first sensor, based on a case in which the measured carbon dioxide concentration in the user's respiration is greater than or equal to a predetermined carbon dioxide concentration, compare each of the user's respiration volume and respiration cycle with a predetermined respiration volume and a predetermined respiration cycle, and based on the comparison result, output an alarm signal corresponding to each state of an awakening state or a sleeping state in response to a case that the user is determined to be in the awakening state or the sleeping state.

In response to a case in which the user's respiration volume is greater than the predetermined respiration volume and the user's respiration cycle is longer than the predetermined respiration cycle, the controller may be configured to output a first alarm signal based on a difference between a user's heart temperature and a user's facial temperature being less than a predetermined temperature difference.

The vehicle may further include an Audio Video Navigation (AVN) and a cluster. The controller may be configured to output the first alarm signal including at least one of an operation of outputting a warning screen through the AVN, an operation of outputting a warning screen through the cluster, an operation of transmitting a vibration to a handle, or an operation of transmitting a vibration to a user's seat.

The first sensor may be configured to measure a respiration volume per minute and a respiration rate per minute. The controller may be configured to output a second alarm signal based on a case in which the respiration volume per minute is less than a predetermined first respiration volume per minute, and the respiration rate per minute is less than a predetermined first respiration rate per minute.

Based on the case where the respiration volume per minute is less than the predetermined first respiration volume per minute, and the respiration rate per minute is less than the predetermined first respiration rate per minute, the controller may be configured to output the second alarm signal including at least one of an operation of opening a window of the vehicle or an operation of sounding a warning buzzer.

Based on the case where the respiration volume per minute is less than a predetermined second respiration volume per minute, and the respiration rate per minute is less than a predetermined second respiration rate per minute, the controller may be configured to control to transmit state information data of the user to an emergency center by determining the user's state as a dangerous state.

The controller may be configured to, based on a starting of the vehicle, calculate the respiration volume and the respiration cycle of the user for a predetermined time, and determine the calculated respiration volume and respiration cycle of the user as the predetermined respiration volume and the predetermined respiration cycle.

According to another embodiment of the disclosure, there is provided a method of controlling a vehicle including measuring, by a first sensor, a user's respiration temperature, a user's facial temperature, and a user's heart temperature, measuring, by a second sensor, a carbon dioxide concentration in a user's respiration, determining, by a controller, a user's respiration volume and respiration cycle, based on a case in which the measured carbon dioxide concentration in the user's respiration is greater than or equal to a predetermined carbon dioxide concentration, comparing, by the controller, each of the user's respiration volume and respiration cycle with a predetermined respiration volume and a predetermined respiration cycle, and based on the comparison result, outputting, by the controller, an alarm signal corresponding to each state of an awakening state or a sleeping state in response to a case that the user is determined to be in the awakening state or the sleeping state.

The outputting of the alarm signal corresponding to each state of the awakening state or the sleeping state may include, in response to a case in which the user's respiration volume is greater than the predetermined respiration volume and the user's respiration cycle is longer than the predetermined respiration cycle, outputting a first alarm signal based on a difference between a user's heart temperature and a user's facial temperature being less than a predetermined temperature difference.

The outputting of the alarm signal corresponding to each state of the awakening state or the sleeping state may include outputting the first alarm signal including at least one of an operation of outputting a warning screen through an Audio Video Navigation (AVN), an operation of outputting a warning screen through a cluster, an operation of transmitting a vibration to a handle, or an operation of transmitting a vibration to a user's seat.

The method may further include measuring, by the first sensor, a respiration volume per minute and a respiration rate per minute. The outputting of the alarm signal corresponding to each state of the awakening state or the sleeping state may include outputting a second alarm signal based on a case in which the respiration volume per minute is less than a predetermined first respiration volume per minute, and the respiration rate per minute is less than a predetermined first respiration rate per minute.

The outputting of the alarm signal corresponding to each state of the awakening state or the sleeping state may include, based on the case where the respiration volume per minute is less than the predetermined first respiration volume per minute, and the respiration rate per minute is less than the predetermined first respiration rate per minute, outputting the second alarm signal including at least one of an operation of opening a window of the vehicle or an operation of sounding a warning buzzer.

The method may further include, based on the case where the respiration volume per minute is less than a predetermined second respiration volume per minute, and the respiration rate per minute is less than a predetermined second respiration rate per minute, controlling, by the controller, to transmit state information data of the user to an emergency center by determining the user's state as a dangerous state.

The comparing of each of the user's respiration volume and respiration cycle with the predetermined respiration volume and the predetermined respiration cycle may include, based on a starting of the vehicle, calculating the respiration volume and the respiration cycle of the user for a predetermined time, and determining the calculated respiration volume and respiration cycle of the user as the predetermined respiration volume and the predetermined respiration cycle.

BRIEF DESCRIPTION OF THE DRAWINGS

These and/or other features of embodiments of the disclosure will become apparent and more readily appreciated from the following description of the embodiments, taken in conjunction with the accompanying drawings, in which:

FIG. 6 is a flowchart illustrating an operation of determining whether a user's respiration has stopped, according to an embodiment.

DETAILED DESCRIPTION OF ILLUSTRATIVE EMBODIMENTS

Figure 1:
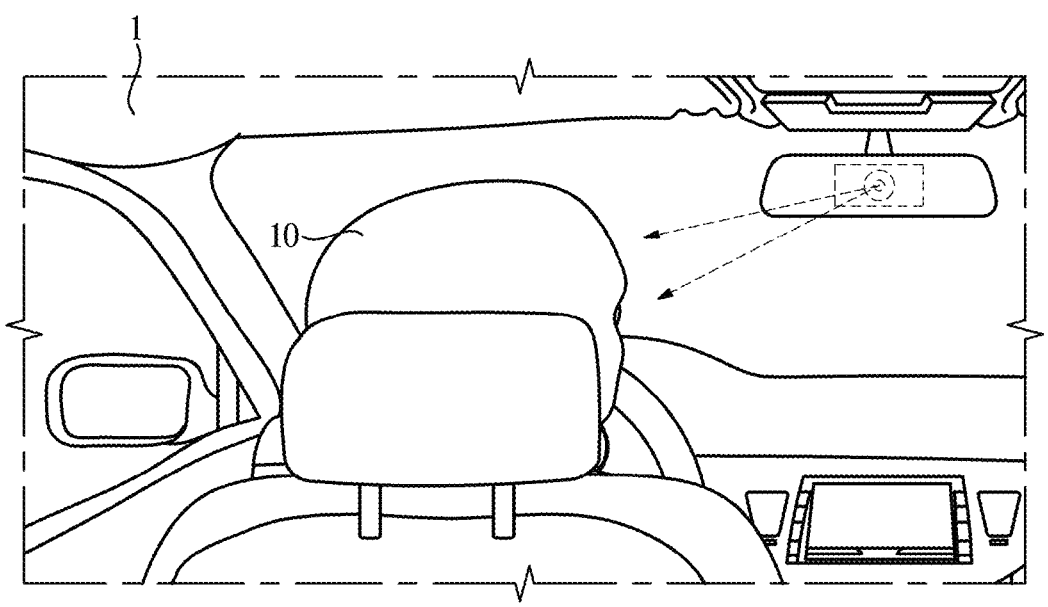
FIG. 1 is a view illustrating an operation of determining a respiration volume and a respiration cycle of a user according to an embodiment.

Like reference numerals refer to like elements throughout the specification. Not all elements of the embodiments of the disclosure will be described, and the description of what are commonly known in the art or what overlap each other in the exemplary embodiments will be omitted. The terms as used throughout the specification, such as "~ part," "~ module," "~ member," "~ block," etc., may be implemented in software and/or hardware, and a plurality of "~ parts," "~ modules," "~ members," or "~ blocks" maybe implemented in a single element, or a single "~ part," "~ module," "~ member," or "~ block" may include a plurality of elements.

It will be further understood that the term "connect" and its derivatives refer both to direct and indirect connection, and the indirect connection includes a connection over a wireless communication network.

The terms "include (or including)" and "comprise (or comprising)" are inclusive or open-ended and do not exclude additional, unrecited elements or method steps, unless otherwise mentioned.

Further, when it is stated that a layer is "on" another layer or substrate, the layer may be directly on another layer or substrate or a third layer may be disposed therebetween.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section.

It is to be understood that the singular forms "a," "an," and "the" include plural references unless the context clearly dictates otherwise.

Reference numerals used for method steps are merely used for convenience of explanation, but not to limit an order of the steps. Thus, unless the context clearly dictates otherwise, the written order may be practiced otherwise.

Hereinafter, an operation principle and embodiments of the disclosure will be described with reference to accompanying drawings.

Figure 2:
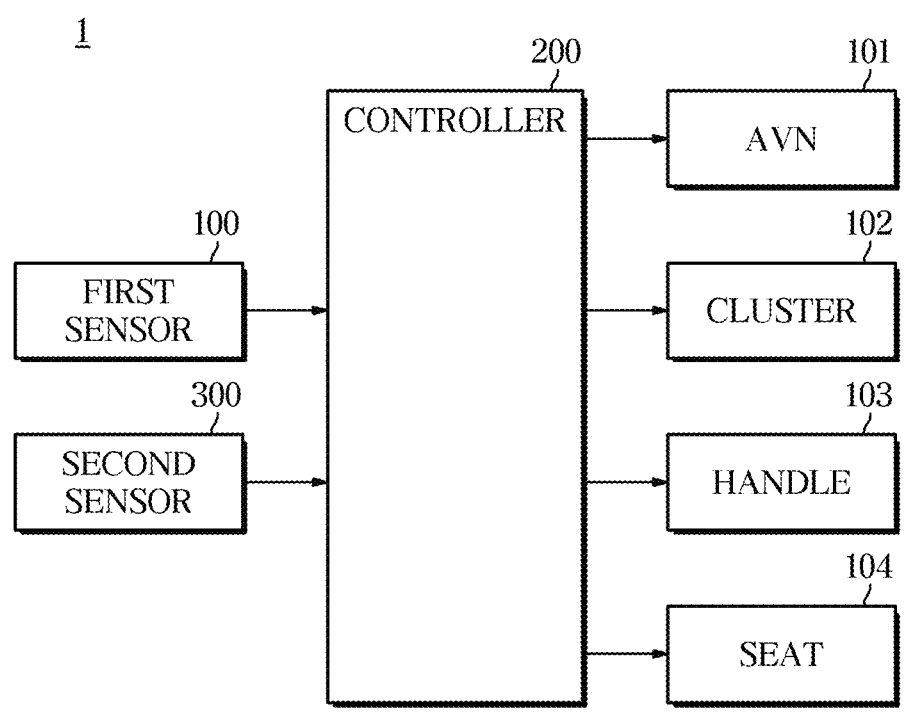
FIG. 2 is a view illustrating a control configuration of a vehicle according to an embodiment.

FIG. 1 is a view illustrating an operation of determining a respiration volume and a respiration cycle of a user according to an embodiment, and FIG. 2 is a view illustrating a control configuration of a vehicle according to an embodiment.

Referring to FIGS. 1 and 2, a vehicle 1 may include a first sensor 100 that measures a user 10's respiration temperature, the user 10's facial temperature, and the user 10's heart temperature, a second sensor 300 that measures a carbon dioxide concentration in the user 10's respiration, and a controller 200.

The controller 200 may determine a user's respiration volume and respiration cycle based on the first sensor 100. When the measured carbon dioxide concentration in the user's respiration is greater than or equal to a predetermined carbon dioxide concentration, the controller 200 may compare the user's respiration volume and respiration cycle with a predetermined respiration volume and a predetermined respiration cycle, and may output an alarm signal according to each state to the user when it is determined that the user is in an awakening state before sleep or a sleeping state.

In addition, the vehicle may include an Audio Video Navigation (AVN) 101 and a cluster 102.

The first sensor 100 and the second sensor 300 may be included in a camera together. Only one of the first sensor 100 or the second sensor 300 may be embedded in the camera, and the other may be installed at another position in the vehicle 1. The first sensor 100 and the second sensor 300 are not limited to positions inside the camera. The first sensor 100 may mean a thermal imaging camera.

The first sensor 100 may measure a temperature of a user's heart, which is a temperature near the user's heart, and a temperature of a user's face, and may measure a temperature of the user's inhalation and exhalation. A specific operation will be described later.

The second sensor 300 may refer to a sensor for measuring the carbon dioxide concentration. The carbon dioxide concentration measurement sensor may use $CO_2$ NDIR (non-dispersive infrared) or $CO_2$ IR (infrared), and may be a commonly used carbon dioxide measurement sensor. Normal carbon dioxide in the atmosphere corresponds to approximately 0.03%, but in a case of human exhalation, it corresponds to approximately 4% on average, and in a case of human inhalation, it corresponds to 0.03% carbon dioxide, which distinguishes the user's respiration from an air in the atmosphere. Even if the carbon dioxide concentration is not 4%, the carbon dioxide concentration can be different for each person, so the vehicle 1 may pre-measure and store the carbon dioxide concentration according to the user's respiration.

The vehicle 1 may measure and store not only the carbon dioxide concentration, but also a normal respiration rate, a normal respiration cycle, a respiration rate per minute, and a respiration volume per minute before the user enters the awakening state or the sleeping state. Before the user falls into the awakening state or the sleeping state, information about the normal respiration rate, the normal respiration cycle, the respiration rate per minute, the respiration volume per minute, etc. maybe stored in advance in a storage, or maybe stored using various devices in addition to the storage.

The controller 200 may output a notification signal according to each state when it is determined that the user is in the awakening state or the sleeping state. The awakening state before sleep may refer to a specific state just before the person enters the sleeping state. The sleeping state may refer to a state in which the person has fallen asleep, and may refer to sleeping in a rapid eye movement sleep (REM) state or a non-rapid eye movement sleep (REM) state.

The controller 200 may output an alarm signal through the cluster 102 and the AVN 101, and may also output a signal through a HUD. The controller 200 may also output the alarm signal that vibrates a handle 103, a seat 104, and the like. In addition, the controller 200 may reduce the carbon dioxide concentration by opening a window of the vehicle 1 or introducing an outside air through a Full Automatic Temperature Control (FATC) mode.

In a case of an autonomous vehicle, it may include a device for autonomously controlling the vehicle 1 to move to a safe position.

In addition, when it is determined that the user is in a respiration stop state, the controller 200 may transmit a user's crisis state information data to inform an emergency center of a user's crisis state through a telephone management system (TMS).

The controller 200 may determine the user's respiration volume and respiration cycle based on the user's respiration temperature, the user's facial temperature, the user's heart temperature, and the carbon dioxide concentration in the user's respiration obtained from the first sensor 100 and the second sensor 300. The controller 200 may compare this with the predetermined respiration volume and the predetermined respiration cycle to determine whether the user corresponds to the awakening state or the sleeping state, and may output the alarm signal according to the user's state.

The predetermined respiration volume and the predetermined respiration cycle may be determined based on measured or stored data of the respiration volume and the respiration cycle at a time of the user's usual awakening state or sleeping state.

In addition, the predetermined respiration volume and the predetermined respiration cycle maybe determined as the user's respiration volume and respiration cycle for a predetermined time in an initial stage after the user turns on the vehicle 1. The predetermined time may be set in advance, and may be determined based on the user's respiration volume and respiration cycle. Particularly, the controller 200 may calculate the respiration volume and the respiration rate based on the carbon dioxide concentration in the user's respiration in the initial stage obtained from the first sensor 100 and the second sensor 300, and determine this as the predetermined respiration volume and the predetermined respiration cycle. The controller 200 may also determine the respiration stop state by measuring the user's respiration rate per minute and respiration volume per minute. The controller 200 may determine the user's respiration rate per minute and respiration volume per minute based on the user's respiration temperature, the user's facial temperature, the user's heart temperature, and the carbon dioxide concentration in the user's respiration obtained from the first sensor 100 and the second sensor 300. The operation of determining the user's respiration state will be described in detail later.

The controller 200 is a processor that controls all operations of the vehicle 1, and may be a processor of an electronic control unit (ECU) that controls overall operations of the power system. In addition, the controller 200 may control operations of various modules and devices built into the vehicle 1. According to an embodiment, the controller 200 may generate control signals for controlling various modules, devices, etc. built in the vehicle 1 to control the operation of each component.

In addition, the controller 200 may include a memory in which programs that perform operations described above and below and various data related thereto are stored, and a processor that executes programs stored in the memory. In addition, the controller 200 may be integrated into a System on Chip (SOC) built into the vehicle 1 and may be operated by the processor. However, since there is not only one SOC embedded in the vehicle 1, but may be a plurality of SOCs, it is not limited to being integrated into only one SOC.

The controller 200 may be implemented through at least one type of storage medium such as flash memory type, hard disk type, multimedia card micro type, card type of memory (e.g. SD or XD memory, etc.), RAM (Random Access Memory), SRAM (Static Random Access Memory), ROM (Read-Only Memory), EEPROM (Electrically Erasable Programmable Read-Only Memory), PROM (Programmable Read-Only Memory), magnetic memory, or magnetic disk. However, it is not limited thereto, and may be implemented in any other form known in the art.

At least one component may be added or omitted to correspond to the performances of the components of the vehicle 1 illustrated in FIG. 2. In addition, the mutual positions of the components may be changed to correspond to the performance or structure of the system.

Some of the components illustrated in FIG. 2 may refer to a software component and/or a hardware component, such as a Field Programmable Gate Array (FPGA) and an Application Specific Integrated Circuit (ASIC).

Figure 3:
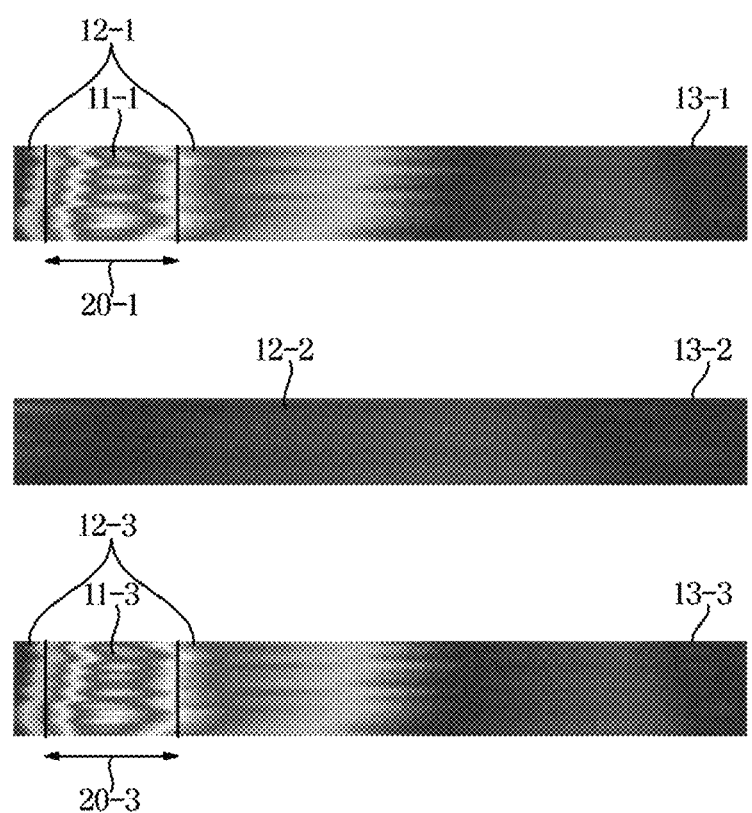
FIG. 3 is a view illustrating an operation of calculating a respiration volume and a respiration cycle through an image analysis captured by a camera according to an embodiment.

FIG. 3 is a view illustrating an operation of calculating a respiration volume and a respiration cycle through an image analysis captured by a camera according to an embodiment.

Referring to FIG. 3 in detail, an air temperature of the exhalation exhaled by the user 10 and the inhalation inhaled by the user 10 may be detected through the first sensor 100. Looking at an uppermost image 13-1, the temperature of exhalation exhaled by the user may be measured by the first sensor 100, and particularly, a color difference occurs in the image captured by the thermal imaging camera according to the temperature. The user's respiration volume may be determined by a length 20-1 of a certain part 11-1 on a left side of the image. When the respiration volume is large, the length 20-1 of the certain part 11-1 on the left side of the image increases. When the respiration volume is small, the length 20-1 of the certain part 11-1 on the left side of the image decreases. The user's respiration cycle may be determined by checking a time when the user's inhalation or exhalation is measured. When the user inhales, the temperature is lower than that of the exhalation, so the certain part 11-1 on the left on the uppermost image that was detected in the exhalation, such as the middle image 13-2, is not detected or is detected finely. When the user exhales again after the user inhales, the first sensor 100 may detect the same temperature as shown in the lowermost image 13-3 (referring to a length 20-3 of a certain part 11-3 on a left side of the image. At this time, a time taken from the inhalation to a next inhalation may be measured to determine the user's respiration cycle. The user's respiration cycle may also be determined by measuring a time taken from the exhalation to a next exhalation. In addition, the first sensor 100 and the second sensor 300 may be used to determine the user's respiration volume and the user's respiration cycle by using various methods commonly used.

Figure 4:
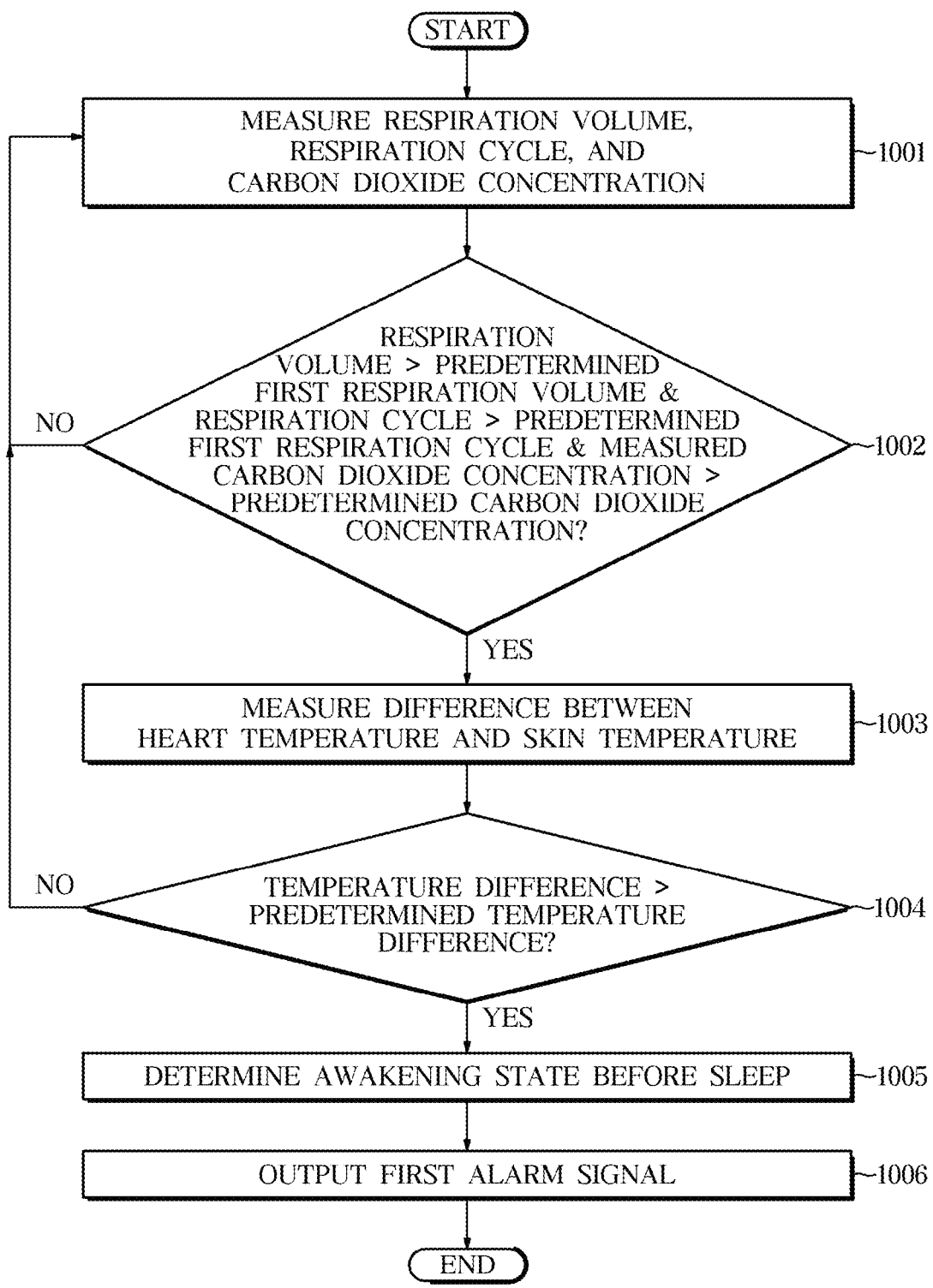
FIG. 4 is a flowchart illustrating an operation of determining whether a user corresponds to an awakening state according to an embodiment.

FIG. 4 is a flowchart illustrating an operation of determining whether a user corresponds to an awakening state according to an embodiment.

Referring to FIG. 4 in detail, the controller 200 may determine whether the user corresponds to the awakening state before sleep and output the alarm signal.

First, the user's respiration volume, respiration cycle, and carbon dioxide concentration may be measured in the manner described in FIG. 3 (1001).

The predetermined carbon dioxide concentration may refer to a reference value necessary to determine that it is the user's respiration. Subsequently, the measured respiration volume, respiration cycle, and carbon dioxide concentration are compared with a predetermined first respiration volume, a predetermined first respiration cycle, and a predetermined carbon dioxide concentration (1002). The predetermined first respiration volume and the predetermined first respiration cycle may refer to a reference value of a predetermined respiration volume and respiration cycle in order for the user to determine the awakening state before sleep.

When the measured carbon dioxide concentration value is greater than the predetermined carbon dioxide concentration, the user's respiration volume is less than the predetermined respiration volume, or the user's respiration cycle is shorter than the first predetermined respiration cycle, the controller 200 may measure the user's respiration volume and respiration cycle again (1001).

When the user's respiration volume is greater than the predetermined respiration volume value and the user's respiration cycle is longer than the predetermined first respiration cycle, the controller 200 may measure the heart temperature and a skin temperature in a facial area to measure the difference between the heart temperature and the skin temperature in the facial area (1003).

In a process of reaching the awakening state before sleep, the heart temperature decreases, so the difference between the heart temperature and the facial temperature may decrease. Conversely, the facial temperature may increase, resulting in a smaller difference between the heart temperature and the facial temperature.

After comparing the difference between the heart area and the skin temperature of the facial area with a predetermined temperature difference (1004), when the difference between the heart area and the skin temperature of the facial area is greater than the predetermined temperature difference, the controller 200 may determine that it is not the awakening state before sleep and measure the user's respiration volume and respiration cycle again (1001). When the difference between the heart area and the skin temperature of the facial area is greater than the predetermined temperature difference, the controller 200 may determine the user's state as the awakening state before sleep (1005), and may output a first alarm signal (1006). The predetermined temperature difference may generally refer to the difference between the heart area and the skin temperature of the facial area when the person falls into the awakening state before sleep, and may refer to an average temperature difference between the heart area and the facial area when the user falls into the awakening state before sleep previously stored in the storage. Outputting the first alarm signal may include at least one of an operation of outputting a warning screen through the AVN 101, an operation of outputting the warning screen through the cluster 102, an operation of transmitting the vibration to the handle 103, or an operation of transmitting vibration to the user's seat 104.

Figure 5:
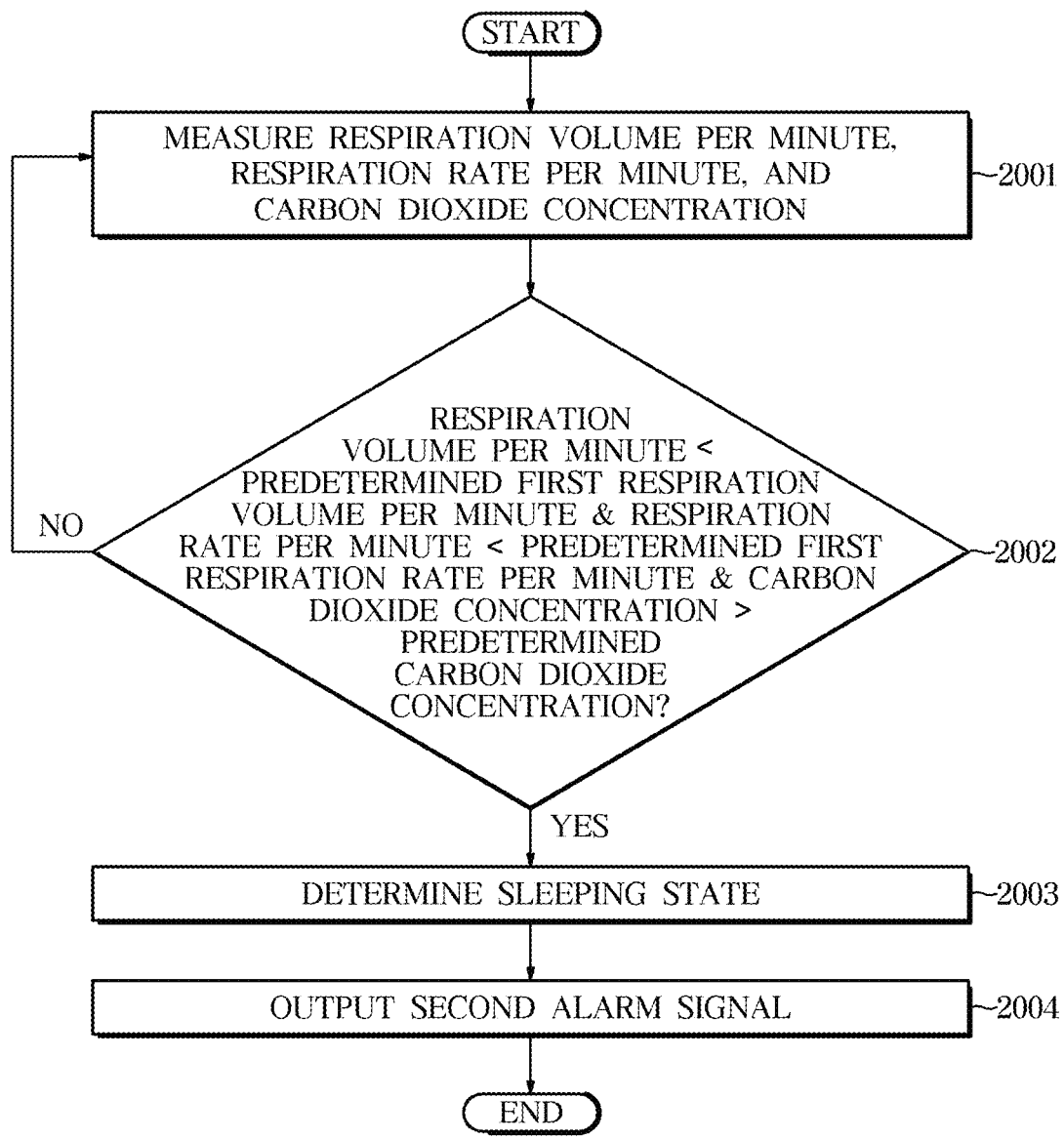
FIG. 5 is a flowchart illustrating an operation of determining whether a user corresponds to a sleeping state according to an embodiment.

FIG. 5 is a flowchart illustrating an operation of determining whether a user corresponds to a sleeping state according to an embodiment.

Referring to FIG. 5 in detail, the controller 200 may measure the user's respiration volume per minute, respiration rate per minute, and the carbon dioxide concentration (2001), and may compare the user's respiration volume per minute, respiration rate per minute, and the carbon dioxide concentration with the predetermined first respiration volume per minute, the predetermined first respiration rate per minute, and the predetermined carbon dioxide concentration (2002).

When the user's respiration volume per minute is greater than the predetermined first respiration volume per minute, or the user's respiration rate per minute is greater than a predetermined first respiration rate per minute or the carbon dioxide concentration is less than the predetermined carbon dioxide concentration, the controller 200 does not determine that the user is in the sleeping state and measures the respiration volume per minute, the respiration rate per minute, and the carbon dioxide concentration again (2001).

When the user's respiration volume per minute is less than the predetermined first respiration volume per minute, the user's respiration rate per minute is less than the predetermined first respiration rate per minute, and the carbon dioxide concentration is greater than the predetermined first carbon dioxide concentration, the controller 200 may determine that the user corresponds to the sleeping state (2003), and may output a second alarm signal to the user (2004). Outputting the second alarm signal may include at least one of an operation of opening a window of the vehicle 1 or an operation of sounding a warning buzzer.

The warning buzzer sound may include a clock and a speaker. In addition, the second alarm may simultaneously perform an operation of a first alarm.

FIG. 6 is a flowchart illustrating an operation of determining whether a user's respiration has stopped, according to an embodiment.

Referring to FIG. 6 in detail, the first sensor 100 may measure the respiration volume per minute, the respiration rate per minute, and the carbon dioxide concentration (3001). The respiration volume per minute, the respiration rate per minute, and the carbon dioxide concentration may be compared with a predetermined second respiration volume per minute, a predetermined second respiration rate per minute, and a predetermined carbon dioxide concentration (3002). At this time, when the respiration volume per minute is less than the predetermined second respiration volume per minute, the controller 200 may measure the respiration rate per minute next to the user's state. When the measured respiration rate per minute is also less than the predetermined second respiration rate per minute, and the carbon dioxide concentration is higher than the predetermined carbon dioxide concentration, the controller 200 may determine as the respiration stop state (3003). The predetermined second respiration volume per minute and the predetermined second respiration per minute may refer to the respiration volume per minute and the respiration rate per minute of a person who is unable to breathe in general. In general, the respiration volume per minute and the respiration rate per minute of the person who is unable to breathe may be zero or a value close to zero. When it is determined that the user's respiration is stopped, the controller 200 may determine the user's state as a dangerous state and control the user's state information data to be transmitted to the emergency center (3004). Even if the respiration volume per minute and the respiration rate per minute are not zero, if it is determined that the respiration is not felt, the controller 200 may control the user's state to be transmitted to the emergency center. In addition to transmitting the user's state information to the emergency center, autonomous vehicles may also move the vehicle 1 to a safe position.

According to the embodiments of the disclosure, the vehicle and the method of controlling the vehicle may calculate the user's respiration cycle and respiration volume through the camera, determine whether the user falls into the sleeping state, and output the alarm signal when the user falls into the sleeping state to prevent a traffic accident to the user in advance.

The disclosed embodiments may be implemented in the form of a recording medium storing computer-executable instructions that are executable by a processor. The instructions may be stored in the form of a program code, and when executed by a processor, the instructions may generate a program module to perform operations of the disclosed embodiments. The recording medium may be implemented as a non-transitory computer-readable recording medium.

The non-transitory computer-readable recording medium may include all types of recording media storing commands that may be interpreted by a computer. For example, the non-transitory computer-readable recording medium may be, for example, ROM, RAM, a magnetic tape, a magnetic disc, flash memory, an optical data storage device, and the like.

Embodiments of the disclosure have thus far been described with reference to the accompanying drawings. It should be apparent to those of ordinary skill in the art that the disclosure may be practiced in other forms than the embodiments as described above without changing the technical idea or essential features of the disclosure. The above embodiments are only by way of example, and should not be interpreted in a limited sense.

What is claimed is:

1. A vehicle comprising:
   a first sensor configured to measure a respiration temperature, a facial temperature, and a heart temperature of a user;
   a second sensor configured to measure a carbon dioxide concentration in a respiration of the user; and
   a controller configured to:
     determine a respiration volume and a respiration cycle of the user based on measurements of the first sensor;
     based on the measured carbon dioxide concentration in the respiration being greater than or equal to a predetermined carbon dioxide concentration, compare each of the respiration volume and the respiration cycle with a predetermined respiration volume and a predetermined respiration cycle; and
     based on the comparison result, output an alarm signal corresponding to each state of an awakening state or a sleeping state in response to a determination that the user is in the awakening state or the sleeping state.

2. The vehicle according to claim 1, wherein, in response to the respiration volume being greater than the predetermined respiration volume and the respiration cycle being longer than the predetermined respiration cycle, the controller is configured to output a first alarm signal based on a difference between the heart temperature and the facial temperature being less than a predetermined temperature difference.

3. The vehicle according to claim 2, further comprising:
   an Audio Video Navigation (AVN); and
   a cluster;
   wherein the controller is configured to output the first alarm signal by an operation of outputting a warning screen through the AVN, an operation of outputting a warning screen through the cluster, an operation of transmitting a vibration to a handle, or an operation of transmitting a vibration to a seat of the user.

4. The vehicle according to claim 1, wherein:
   the first sensor is configured to measure a respiration volume per minute and a respiration rate per minute; and
   the controller is configured to output a second alarm signal based on the respiration volume per minute being less than a predetermined first respiration volume per minute, and the respiration rate per minute being less than a predetermined first respiration rate per minute.

5. The vehicle according to claim 4, wherein, based on the respiration volume per minute being less than the predetermined first respiration volume per minute, and the respiration rate per minute being less than the predetermined first respiration rate per minute, the controller is configured to output the second alarm signal including an operation of opening a window of the vehicle or an operation of sounding a warning buzzer.

6. The vehicle according to claim 4, wherein, based on the respiration volume per minute being less than a predetermined second respiration volume per minute, and the respiration rate per minute being less than a predetermined second respiration rate per minute, the controller is configured to control to transmit state information data of the user to an emergency center by determining a state of the user as a dangerous state.

7. The vehicle according to claim 1, wherein the controller is configured to:
based on a starting of the vehicle, calculate the respiration volume and the respiration cycle of the user for a predetermined time; and
determine the calculated respiration volume and the calculated respiration cycle of the user as the predetermined respiration volume and the predetermined respiration cycle.

8. A method of controlling a vehicle, the method comprising:
measuring a respiration temperature, a facial temperature, and a heart temperature of a user;
measuring a carbon dioxide concentration in a respiration of the user;
determining a respiration volume and respiration cycle of the user;
determining that the measured carbon dioxide concentration in the respiration is greater than or equal to a predetermined carbon dioxide concentration;
comparing each of the respiration volume and the respiration cycle with a predetermined respiration volume and a predetermined respiration cycle; and
based on the comparison result, outputting an alarm signal corresponding to each state of an awakening state or a sleeping state in response to the user being determined to be in an awakening state or a sleeping state.

9. The method according to claim 8, wherein outputting the alarm signal corresponding to each state of the awakening state or the sleeping state comprises, in response to the respiration volume being greater than the predetermined respiration volume and the respiration cycle being longer than the predetermined respiration cycle, outputting a first alarm signal based on a difference between the heart temperature and the facial temperature being less than a predetermined temperature difference.

10. The method according to claim 9, wherein outputting the alarm signal corresponding to each state of the awakening state or the sleeping state comprises outputting the first alarm signal including an operation of outputting a warning screen through an Audio Video Navigation (AVN), an operation of outputting a warning screen through a cluster, an operation of transmitting a vibration to a handle, or an operation of transmitting a vibration to a seat of the user.

11. The method according to claim 8, further comprising measuring a respiration volume per minute and a respiration rate per minute, wherein outputting the alarm signal corresponding to each state of the awakening state or the sleeping state comprises outputting a second alarm signal based on the respiration volume per minute being less than a predetermined first respiration volume per minute, and the respiration rate per minute being less than a predetermined first respiration rate per minute.

12. The method according to claim 11, wherein outputting the alarm signal corresponding to each state of the awakening state or the sleeping state comprises, based on the respiration volume per minute being less than the predetermined first respiration volume per minute, and the respiration rate per minute being less than the predetermined first respiration rate per minute, outputting the second alarm signal including an operation of opening a window of the vehicle or an operation of sounding a warning buzzer.

13. The method according to claim 11, further comprising based on the respiration volume per minute being less than a predetermined second respiration volume per minute, and the respiration rate per minute being less than a predetermined second respiration rate per minute, controlling to transmit state information data of the user to an emergency center by determining a state of the user as a dangerous state.

14. The method according to claim 8, wherein comparing each of the respiration volume and the respiration cycle with the predetermined respiration volume and the predetermined respiration cycle comprises:
based on a starting of the vehicle, calculating the respiration volume and the respiration cycle of the user for a predetermined time; and
determining the calculated respiration volume and the calculated respiration cycle of the user as the predetermined respiration volume and the predetermined respiration cycle.

15. A system for alerting a user during driving of a vehicle, the system comprising:
a first sensor installed in a vehicle and configured to measure a respiration temperature, a facial temperature, and a heart temperature of the user;
a second sensor installed in the vehicle and configured to measure a carbon dioxide concentration in a respiration of the user; and
a controller coupled to the first sensor and the second sensor, the controller configured to:
determine a respiration volume and a respiration cycle of the user based on measurements of the first sensor;
based on the measured carbon dioxide concentration in the respiration being greater than or equal to a predetermined carbon dioxide concentration, compare each of the respiration volume and the respiration cycle with a predetermined respiration volume and a predetermined respiration cycle; and
based on the comparison result, output an alarm signal corresponding to an awakening state or a sleeping state in response to a determination that the user is in the awakening state or the sleeping state.

16. The system according to claim 15, wherein:
in response to the respiration volume being greater than the predetermined respiration volume and the respiration cycle being longer than the predetermined respiration cycle, the controller is configured to output a first alarm signal based on a difference between the heart temperature and the facial temperature being less than a predetermined temperature difference; and
the controller is configured to output the first alarm signal by an operation of outputting a warning screen through an Audio Video Navigation of the vehicle, an operation of outputting a warning screen through a cluster of the vehicle, an operation of transmitting a vibration to a handle of the vehicle, or an operation of transmitting a vibration to a seat of the user in the vehicle.

17. The system according to claim 15, wherein:
the first sensor is configured to measure a respiration volume per minute and a respiration rate per minute; and
the controller is configured to output a second alarm signal based on the respiration volume per minute being less than a predetermined first respiration volume per minute, and the respiration rate per minute being less than a predetermined first respiration rate per minute.

18. The system according to claim 17, wherein, based on the respiration volume per minute being less than the predetermined first respiration volume per minute, and the respiration rate per minute being less than the predetermined first respiration rate per minute, the controller is configured to output the second alarm signal including an operation of opening a window of the vehicle or an operation of sounding a warning buzzer in the vehicle.

19. The system according to claim 17, wherein, based on the respiration volume per minute being less than a predetermined second respiration volume per minute, and the respiration rate per minute being less than a predetermined second respiration rate per minute, the controller is configured to control to transmit state information data of the user to an emergency center by determining a state of the user as a dangerous state.

20. The system according to claim 15, wherein the controller is configured to:
- based on a starting of the vehicle, calculate the respiration volume and the respiration cycle of the user for a predetermined time; and
- determine the calculated respiration volume and the calculated respiration cycle of the user as the predetermined respiration volume and the predetermined respiration cycle.

\* \* \* \* \*